United States Patent [19]

Gainsley et al.

[11] Patent Number: 4,671,289

[45] Date of Patent: Jun. 9, 1987

[54] HOUSING FOR ULTRASONIC DETECTOR

[75] Inventors: James D. Gainsley, St. Louis Park; David M. Vikre, Coon Rapids; Jack E. Larsen, Champlin; William F. Hursh, Minneapolis, all of Minn.; David L. Carlson, Ames, Iowa

[73] Assignee: Renco Corporation, Minneapolis, Minn.

[21] Appl. No.: 796,748

[22] Filed: Nov. 8, 1985

[51] Int. Cl.[4] .................................................. A61B 10/00
[52] U.S. Cl. ...................................... 128/660; 200/157; 200/333
[58] Field of Search .................... 128/660-663; 200/157, 333, 302.1, 302.2

[56] References Cited

U.S. PATENT DOCUMENTS

| Re. 29,047 | 11/1976 | Brindley | 200/302.2 X |
|---|---|---|---|
| 3,126,467 | 3/1964 | Stevens | 200/302.2 |
| 3,822,372 | 7/1974 | Coenen et al. | 200/157 |
| 3,870,843 | 3/1975 | Witte | 200/302.2 |
| 3,911,241 | 10/1975 | Jarrard | 200/157 |
| 4,112,927 | 9/1978 | Carlson | 128/660 |
| 4,138,999 | 2/1979 | Eckhart et al. | 128/660 |
| 4,226,229 | 10/1980 | Eckhart et al. | 128/660 |
| 4,352,968 | 10/1982 | Pounds | 200/302 |
| 4,356,367 | 10/1982 | Moldenhauer | 200/157 X |
| 4,359,055 | 11/1982 | Carlson | 128/660 |
| 4,359,056 | 11/1982 | Carlson | 128/660 |
| 4,389,550 | 6/1983 | Reiter | 200/333 X |

Primary Examiner—Kyle L. Howell
Assistant Examiner—Francis J. Jaworski
Attorney, Agent, or Firm—Merchant, Gould, Smith, Edell, Welter & Schmidt

[57] ABSTRACT

A housing is disclosed for an apparatus for determining pregnancy in animals which includes a pressure activated switch. The housing includes a housing portion formed from integrally molded synthetic plastic which is selected to have a rigidity which varies with the thickness of the material. The handle includes walls which define a chamber for receiving components of the apparatus including a pressure activated switch. The walls are selected to have material thickness sufficient for the walls to be rigid in response to a pressure applied by an operator's hand. A digit engaging portion of one of the walls is provided with a reduced thickness sufficient for the digit engaging portion to flex into the chamber in response to a pressure applied by an operator's hand and returned to a rest position when pressure is withdrawn. The pressure activated switch is included within the chamber and has a pressure activated element opposing the digit engaging portion.

26 Claims, 4 Drawing Figures

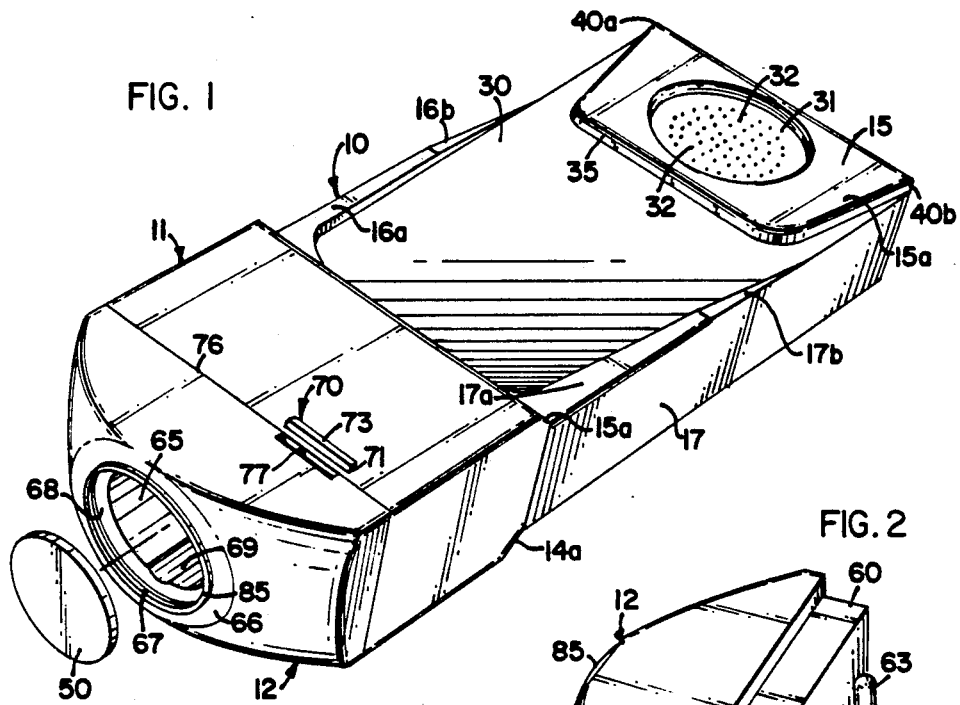
FIG. 1
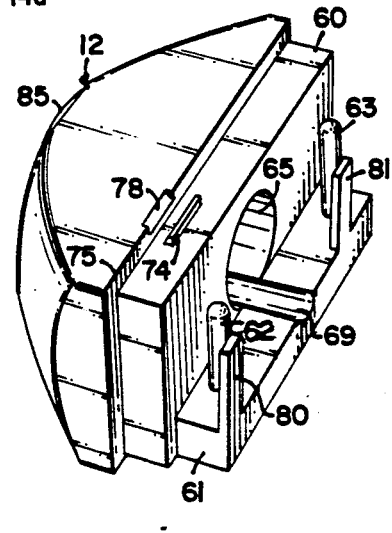
FIG. 2
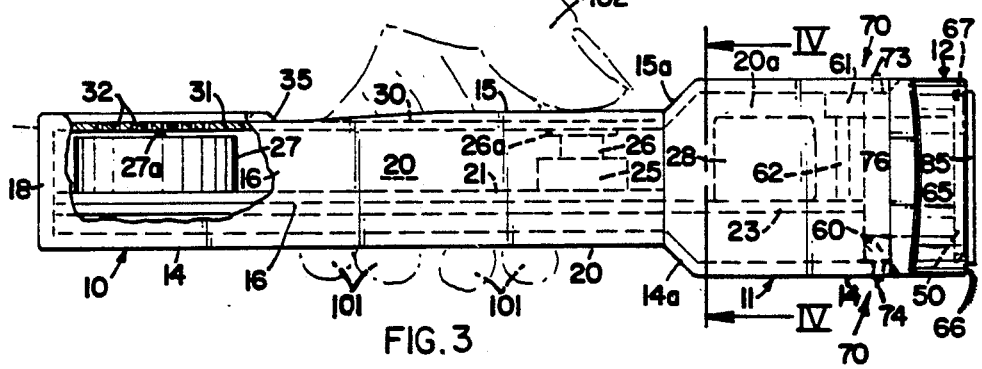
FIG. 4
FIG. 3

HOUSING FOR ULTRASONIC DETECTOR

BACKGROUND OF THE INVENTION

I. Field of the Invention

This invention pertains to ultrasonic testing apparatus for determining pregnancy in animals. More particularly, this invention pertains to housings for such apparatus.

II. Description of the Prior Art

In the prior art, methods have been developed in the field of animal husbandry in which ultrasonic pulsing and detection have been used for detecting pregnancies in sows and other farm animals. For many reasons, it may be economically important for a livestock producer to know if an individual farm animal is pregnant. Such knowledge may be required in order to make a decision as to whether to market the animal, whether to start it on a special feeding program, or whether to rebreed the animal during the same season.

Ultrasonic pregnancy detectors of the prior art include detectors having ultrasonic transducers which are placed against the abdomen of the animal to be tested. For proper ultrasonic pulse propagation, the end of the transducer which is placed against the animal's abdomen is first dipped in water, mineral oil or motor oil before placing it against the animal's body.

The prior art detection apparatus includes circuits for pulsing the transducer and processing echoes detected by the transducer. The processed signals include an output which may be displayed to an operator either visually or audibly and which indicate the pregnant condition of the animal being tested. An example of such a prior art apparatus with circuitry for performing the above tasks includes commonly assigned U.S. Pat. No. 4,112,927 to Carlson dated Sept. 12, 1978. As shown in the patent, the apparatus includes an instrument housing 10 with a probe 11 comprising an ultrasonic transducer 12 connected by means of an electrical cable 13 to the housing 10. The patent discloses two methods of indicating the output to an operator. The first is a visual display which shows an oscilliscope trace. The patent also teaches circuitry for generating an audible tone in which, in the embodiment shown, a signal tone indicates a strong return signal from the animal's uterus while the absence of a tone indicates that the animal is not pregnant.

While the apparatus described has been of value to the animal husbandry industry, certain difficulties are encountered in the use of the apparatus. Namely, the animal under observation is often uncooperative and may be attempting to squirm away from the operator during the period of observation. Indeed, the animal may attempt to attack the probe or the operator. In addition to the adverse circumstances generated by the violence of the animal under observation, the environment in which the apparatus is used presents certain difficulties. For example, the apparatus must be subjected to contact with mineral oil or the like which is used in the testing procedure as well as the often dirty environment of the test site due to animal waste and dust. Finally, the livestock producer needs an apparatus which can be wielded easily by the operator while the operator is attempting to control the animal under observation. Therefore, while the circuitry of the prior art has proved generally satisfactory, there is a need for improvement of apparatus housing to permit its ease of use by an operator while providing for protection from the adverse environment in which it is used.

SUMMARY OF THE PRESENT INVENTION

According to a preferred embodiment of the present invention, there is provided a housing for an ultrasonic detection apparatus where the apparatus includes a transducer, a pressure activated switch, circuitry and an audible sounder. The housing is formed of integrally molded synthetic plastic material including a back wall and a spaced-apart front wall joined by side walls and an end wall. The walls define a cavity for receiving circuit components including the sounder with its sound generating surface opposing the front wall at the back end of the handle and a pressure activated switch with its actuating element opposing the front wall. The synthetic material is selected from a material which has a rigidity varying with its thickness with the back wall, side walls and end walls made of material having sufficient thickness such that the walls are rigid. The front wall includes a digit engaging portion having an area covering the pressure activated switch with the digit engaging area sufficiently thin for the area to flex in response to a pressure applied on the surface by an operator. When an operator engages a portion of the digit receiving portion, the entire digit receiving portion flexes and engages the pressure activated switch. As a result, the operator can handle the apparatus without having to precisely locate the apparatus within his hand and without having to look at the apparatus during its use. The portion of the front surface opposing the sounder is also provided with a reduced thickness and with a plurality of holes extending through the surface to reduce resistance to sound passing from the sounder.

BRIEF DESCRIPTION OF THE DRAWINGS

FIG. 1 is a perspective view of a housing according to the present invention;

FIG. 2 is a perspective view of a cap for the housing;

FIG. 3 is a side view of the housing of FIG. 1; and

FIG. 4 is a view taken along lines IV—IV of FIG. 3.

DESCRIPTION OF THE PREFERRED EMBODIMENT

As shown in FIG. 1, the housing of the present invention includes a handle portion 10 having an enlarged portion 11 and a detachable cap 12. The handle 10 and its enlarged portion 11 are integrally formed from molded synthetic plastic material such as a polymer of polypropylene as will be described. The handle 10 includes a back wall 14 and an opposing front wall 15. Front wall 15 is spaced away from back wall 14 and connected thereto by a pair of side walls 16 and 17 and an end wall 18. End wall 18 cooperates with the side walls 16 and 17, front wall 15 and back wall 14 to define a component receiving chamber 20 having an open end opposite end wall 18. Ramps 14a and 15a project outwardly from back wall 14 and front wall 15, respectively, such that front wall 15, back wall 14 and side walls 16 and 17 define a component receiving chamber 20a in the enlarged portion 11 having a cross section greater than that of chamber 20. As will be more fully described, cap 12 is detachably secured to the enlarged portion 11 such that chambers 20 and 20a are closed.

With reference to FIGS. 3 and 4, it can be seen handle portion 10 is provided with integrally molded longitudinally extending spaced-apart rails 21 and 121 on an interior surface of side wall 16. Likewise, side wall 17 is provided with parallel spaced-apart longitudinally extending rails 21a and 121a which are aligned with rails 21 and 121, respectively. The spaced-apart rails define longitudinally extending transversely aligned slots 22 and 22a sized to receive a circuit board 23 extending between the slots. The circuit board contains circuitry for processing signals from a transducer and generating an output indicating pregnancy of an animal. The circuitry itself forms no part of this invention and may be such as that shown in the aforementioned U.S. Pat. No. 4,112,927 or any other suitable circuitry.

Mounted on the circuit board 23 is a pressure activated switch 25 having a pressure sensitive element 26 opposing an inner surface of front wall 15 and separated therefrom by means of a foam rubber pad 26a. Also mounted on the circuit board 23 is a sounder 27 having a sound generating surface 27a opposing inner surface of the front wall 15. Circuit elements to large to fit within chamber 20 (such as battery 28) are mounted on the circuit board 23 within chamber 20a of enlarged portion 11.

As shown in FIG. 3, the handle portion 10 is sized to be received within the hand 100 of an operator. The handle portion 10, and enlarged portion 11 are shaped such that an operator when grasping the housing will be able to quickly and automatically grasp the handle portion 10 with the back wall 14 abutting the four adjacent fingers 101 of the operator and with the thumb 102 of the operator opposing the front wall 15. Alternatively, when an operator grasps the handle portion 10, the back wall 14 will abut the heal of the operator's palm with the fingers 101 of the operator engaging the forward wall 15. To accomplish this, the handle portion 10 is rectangular in cross section (as shown in FIG. 4) with the side walls 16 and 17 being substantially narrower than the back wall 14 and front wall 15. Accordingly, when an operator grasps the handle portion 10 one of the side walls 16 or 17 will naturally face the crease of the operator's palm with front wall 15 opposing either the thumb 102 of the operator or the remaining four fingers 101 of the operator. The enlarged portion 11 including ramps 14a and 15a provide a means by which the operator can, through sense of feel, find the handle portion 10.

As shown in the figures, a majority of the area of the front wall of the handle portion 10 is provided with a depression 30 which may conveniently be referred to as a digit engaging portion 30 of the front wall 15. It should be noted the pressure activated switch 25 is disposed with its activating element 26 opposing the front wall 15 within the area of the digit engaging portion 30. Likewise, an area 31 of the front wall 15 is recessed to provide the area 31 opposing the sound generating surface 27a of sounder 27 with a reduced thickness. Also, area 31 is provided with a plurality of sound transmitting holes 32 extending therethrough.

The synthetic material from which the housing is formed is selected to have a rigidity which varies with a thickness of the material. The thickness of the end wall 18, back wall 14 and side walls 16 and 17 are selected to be rigid in response to pressure applied by an operator's hand. The thickness of the digit engaging portion 30 is selected to have a reduced thickness sufficient for the portion to flex toward the back wall 14 in response to pressure applied by an operator's hand and to be elastic to return to the rest position (as shown in the figures) when pressure is withdrawn.

As best seen in FIG. 1, the digit engaging portion 30 has an area which takes up most of the area of the front wall 15 of handle portion 10. The reduced thickness digit engaging portion 30 is not co-extensive with the area of the front wall 15 of handle 10. The front wall 15 includes a first corner section 16a forming an edge with side wall 16 and extending from enlarged portion 11 toward end wall 18. Likewise, a second corner portion 17a is provided forming an edge with side wall 17 and extending from enlarged portion 11 from end wall 18. The first corner portion 16a and second corner portion 17a are both provided with thicknesses of material sufficient for the portions to be rigid. Also, a thick rigid portion 15a surrounds the area 31 covering sounder 27 and presents a wall 35 projecting away from the reduced thickness digit engaging portion 30. The wall 35 extends around the reduced portion 31 and extends toward a corner 406 formed by the junction of side wall 17, end wall 18 and front wall 15. Likewise, an opposite portion of the wall 35 extends to a corner 40a at the juncture of side wall 16, end wall 18 and front wall 15. The front corner portion 16a and second corner portion 17a are provided with tapered surfaces 16b and 17b, respectively, which gradually taper the thickness of the first corner portion 16a and second corner portion 17a to the thickness of the digit engaging portion 30 and spaced from the corners 40a and 40b.

While the area of the digit engaging portion 30 is not co-extensive with the area of the front wall 15, it is desirable to maximize this area to insure the area may be engaged by the thumb or fingers of an operator engaging the handle 10. Therefore, the area of the digit engaging portion 30 is approximately the area which would be covered by the range of motion of an operator's thumb opposing the front wall 15 as shown in FIG. 3. The rigidly thick portions 16a, 17a and 15a provide structural integrity at the corners of the front wall 15 and also provide a liquid directing channel as will be described later.

The wide area of digit engaging portion 30 enhances the flexibility of the area such that when any area of the portion 30 is depressed by the operator, the entire portion 30 will flex and approach the back wall 14. Accordingly, an operator need not accurately locate his thumb or finger to engage the switch 25 and need only apply pressure to the surface of the digit engaging portion 30 confident the flexing of the portion 30 will result in the switch 25 being activated. A preferred material to provide a desired flexibility at practical thicknesses is a copolymer of polypropylene and more precisely the preferred material is El Paso Rexene Polypropylene Medium Impact Co-Polymer No. 14S4A as supplied by the El Paso Rexene Company of El Paso, Tex. This material is preferred not only in that it has desired flexing properties at practical thicknesses and rigidity at practical thicknesses, the material is relatively inert to oils and other contaminants which may be in the vacinity of the apparatus during its use. I have determined at a thickness of about 0.085 inches the material is sufficiently stiff and impact resistant. Preferably, the reduced thicknesses of digit engaging portion 30 and area 31 will be 0.030 inches which provides adequate flexing but still has sufficient thickness of material to avoid puncture of the material. I believe at thicknesses less than 0.020 inches danger of puncture significantly increases.

The opening of the enlarged portion 11 is closed by cap 12 which also houses transducer crystal 50. As shown in FIG. 2, cap 12 includes a base portion 60 which is rectangular in cross section and sized to be snuggly received within enlarged portion 11. An inwardly projecting flange 61 extends inwardly into chamber 20 from base portion 60 and is provided with a pair of spaced-apart pins 62 and 63 which are sized to extend from base portion 61 and abut circuit board 23 when cap 12 is installed onto the enlarged portion 11 as shown in FIG. 3.

The cap 12 is provided with an axially extending bore 65 therethrough which has an axis generally normal to the rectangular cross section of the enlarged portion 11 and handle 10. The bore 65 terminates at an animal engaging surface 66 of the cap 12 which surface 66 is generally flat and perpendicular to the axis of bore 65. A tapered wall 67 at surface 66 is provided to define an enlarged portion of bore 65 having a ledge 68 for supporting transducer crystal 50. The ledge 68 is spaced from surface 66 a distance slightly greater than the thickness of transducer crystal 50. Also, the tapered wall 67 is provided such that in cross section it presents a dovetail shape having a length greater than the diameter of transducer crystal 50. Transducer crystal 50 is fixed against ledge 68 by means of epoxy which is poured into the dovetail channel which sets forming a rigid wedge covering and surrounding transducer crystal 50. A lead receiving channel 69 is provided for passage of electrical leads from crystal 50 to circuitry on board 23.

Enlarged portion 11 and cap 12 are provided with mating elements comprising locks 70. Front wall 15 of enlarged portion 11 is provided with a transversely extending slot 71 therethrough offset from the axis of bore 65. Likewise, (although not shown) back wall 14 of the enlarged portion 11 is provided with a transversely extending slot which is also offset from the axis of the bore 65 and symmetric with slot 71 about the axis. A surface of base 60 which opposes wall 15 is provided with a protruding tab 73 sized to be received within slot 71 when the cap 12 is inserted into the enlarged portion 11. Similarly, a tab 74 is provided on an opposite side of block 60 to be received within the slot formed through back wall 14. Tabs 73 and 74 are angled and the edge 75 of cap 12 which defines a seam 76 between the cap 12 and the enlarged portion 11 is provided with an angled relief 77 disposed adjacent tab 73 and an angled relief 78 disposed adjacent tab 74. Preferably the angled reliefs 77 and 78 are sized to receive a standard screwdriver such as that of a quarter inch screwdriver which may be inserted within the reliefs to pry away the opposing wall of the enlarged portion 11 and facilitate easy removal of tabs from slots and hence removal of cap 12 from the enlarged portion 11.

As shown in FIG. 2, the cap 12 is originally formed with a pair of flat pins 80 and 81. The pins project upwardly from flange 61 and their surfaces are flushed therewith. The surfaces of pins 80 and 81 are also parallel with flat surface 66 at the top end of the cap 12. Pins 80 and 81 facilitate the mounting of the transducer crystal 50 within the cap 12. With pins 80 and 81 mounted on a horizontally flat surface, the upper surface 66 is also horizontal and flat and the crystal 50 is received within a recess defined by the wall 67 and ledge 68 such that it is also horizontal and flat. An epoxy is poured in the recess to fill the space defined between the recess wall 67 and the transducer crystal 50. An epoxy retaining ring 85 is provided circumferentially surrounding the bore 65 and projecting outwardly from surface 66.

Epoxy is flowed into the recess such that it comes to the top of the wall 85. After the epoxy is set, the wall 85 and epoxy are ground down to be flush with surface 66. At this point, pins 80 and 81 are severed from base 61.

In operation of the apparatus, a livestock producer will apply a mineral oil to the abdomen of an animal such as a sow which is to be tested for pregnancy or dip the top of the cap 12 in the oil. While restraining the animal with one hand, the livestock producer can grasp the apparatus with his free hand. Using the ramps 15a and 14a as indicators by which his fingers may sense the location of handle portion 10, the livestock producer can grasp the handle portion 10. Due to the construction of the invention, it is not important whether the digit engaging portion 30 opposes the operator's thumb 102 or the operator's remaining four fingers 101. The operator places the apparatus against the mineral-coated abdomen with the surface 66 abutting the mineral-coated surface of the animal. By simply squeezing the handle, the walls of the handle portion 10 remain rigid except for the digit engaging portion 30. No matter where on the digit engaging portion 30 the operator applies pressure, the entire area will flex such that the area directly opposing the activating element 26 of pressure activated switch 25 will be depressed activating the circuitry. If the circuitry receives a signal indicating pregnancy, the sounder 26 will generate a tone which will pass through the holes 32 and with the reduced thickness of area 31 providing minimum interference with sound passage from the sounder to the operator. As can be seen, the entire apparatus can be used easily with one hand while the other hand restrains an animal. At no time need the operator take his eye of the animal and look to the apparatus during its use. As a result, an animal can be tested for pregnancy quickly and safely.

It can be seen from the foregoing how the objects of the invention have been obtained in a preferred manner. While the foregoing is a preferred embodiment, the scope of the present invention is not intended to be limited to the specific embodiments shown and is intended to include such modifications and alterations as will appear to those skilled in the art. The present invention is intended to only be limited by the scope of the claims as are appended hereto.

What I claim is:

1. A housing for a hand-held apparatus having a pressure activated switch comprising:

a handle portion formed from an integrally molded synthetic plastic material defining a chamber for receiving components of said apparatus including said switch;

said handle portion sized to be received within an operator's hand and having a back side and an opposing front side having a digit engaging portion; wall means connecting said front side with said back side; said sides and wall means cooperating to define said chamber;

said digit engaging portion having an area substantially greater than a contacting area of said pressure activated switch;

a raised ridge (15a, 14a) disposed on said housing and aligned to position an operator's hand in a predetermined position to block sliding movement of said hand and retain said hand in said position with said operator's digits aligned against said digit engaging portion;

said wall means and back side having a thickness sufficient for said wall means and back side to be rigid in response to pressure applied by an operator's hand; said digit engaging portion of said front side having a thickness less than a thickness of said wall means and back side with said digit engaging portion resiliently flexible to flex toward said back side in response to a pressure applied by an operator's hand and return to a rest position when pressure is withdrawn.

2. A housing according to claim 1 wherein said digit engaging portion has an area approximate to a range of motion of an operator's thumb opposing an operator's palm.

3. A housing according to claim 1 comprising a sound passage portion of said handle portion having a reduced thickness sufficient for said area to flex in response to pressure waves generated by a sound generating device; a plurality of holes provided through said reduced thickness portion.

4. A housing according to claim 3 wherein said digit engaging portion and said sound passage portion both comprise separate depressions formed on an outer surface of said front side with a liquid deflecting wall disposed between said depressions and tapered to direct a flow of fluid from said digit engaging portion away from said sound passage portion and off said front side.

5. A housing according to claim 1 wherein said synthetic material is polypropylene polymer.

6. A housing according to claim 5 wherein said material is a copolymer polypropylene polymer.

7. An apparatus for determining pregnancy in animals including detection and indication means having transmitting and receiving means including a transducer for placement against an animal's body for transmitting ultrasonic energy pulses and for receiving return pulses; circuit means for operating said transmitting and receiving means and processing return pulses to generate an output signal indicating a pregnancy state of an animal; pressure activated switch means for activating said circuit means; said detection and indication means also having signal means for receiving said output signal and indicating said pregnancy state of said animal to an operator; and a housing for said detection and indicating means, said housing comprising:

a handle portion formed from an integrally molded synthetic plastic material defining a chamber sized to receive said pressure activated switch means;

an animal engaging portion with means for securing said transducer to said animal engaging portion;

means for securing said animal engaging portion to said handle portion;

said handle portion sized to be received in an operator's hand and having a back side and an opposing front side having a digit engaging portion; wall means connecting said front side with said back side; said sides and wall means cooperating to define said chamber;

said wall means and back side having a thickness sufficient for said wall means and back side to be rigid in response to pressure applied by an operator's hand; said digit engaging portion of said front side having a thickness less than a thickness of said wall means and back side with said digit engaging portion resiliently flexible to flex toward said back side in response to a pressure applied by an operator's hand and return to a rest position when pressure is withdrawn;

means for supporting said pressure activated switch within said chamber with an activating element of said switch opposing an area of said digit engaging portion with said element spaced from said area a distance for said element not to be in activating engagement with said area when said engaging portion is in said rest position and to be in activating engagement with said area when said engaging portion is flexed in response to a pressure applied by an operator.

8. An apparatus according to claim 7 wherein said digit engaging portion has an area substantially greater than said area opposing said switch.

9. An apparatus according to claim 8 wherein said digit engaging portion has an area approximate to a range of motion of an operator's thumb opposing an operator's palm.

10. An apparatus according to claim 7 wherein said signal means comprises a sounder disposed within said chamber and having a sound generating surface opposing a surface of said handle portion, said opposed surface having a plurality of holes therethrough and having a reduced thickness sufficient for said surface to flex in response to pressure waves generated by said sounder.

11. An apparatus according to claim 10 wherein said opposed surface is an area of said front side and said digit engaging portion is disposed between said transducer and said sounder; said digit engaging portion comprising a depression formed on an outer surface of said front side with a liquid deflecting wall disposed between said depression and said surface opposing said sounder; said liquid deflecting wall tapered to direct a flow of liquid from said depression away from said surface opposing said sounder and off said front side.

12. An apparatus according to claim 7 wherein said animal engaging portion comprises a cap sized to cover an opening in said handle exposing said chamber; said cap including an animal engaging surface with walls defining a recess for receiving a transducer; said walls tapered to define a space having a greater volume away from said animal engaging surface with said transducer sized to have a volume less than a volume of said space; epoxy means for securing said transducer in said recess with said epoxy means flowed into space between said transducer and walls and setting to lock said transducer in said recess.

13. An apparatus according to claim 12 wherein said cap is releasably secured to said handle portion by a plurality of snap lock means on opposing sides of said cap and offset from a center of said cap.

14. An apparatus according to claim 7 wherein said synthetic material is a polypropylene polymer.

15. An apparatus according to claim 14 wherein said material is a copolymer polypropylene polymer.

16. An apparatus according to claim 7 comprising a raised ridge (15a, 14a) disposed on said housing between said digit engaging portion and said animal engaging portion.

17. An apparatus according to claim 16 wherein said raised ridge is disposed for an operator's digits to be aligned with said digit engaging portion when said handle portion is grasped by an operator's hand abutting said raised portion.

18. An apparatus for detecting a characteristic of an animal including detection and indication means having transmitting and receiving means for transmitting a signal to an animal and receiving a response signal, circuit means for operating said transmitting and receiving means and processing said response signal to generate an output signal indicating a characteristic of said animal, pressure activated switch means for activating said circuit means; signal means responsive to said output signal for indicating said characteristic to an operator, a housing for said detection and indication means comprising:

a handle portion formed from an integrally molded synthetic plastic material defining a chamber sized to receive said pressure activated switch means;

a first portion with means for securing said transmitting and receiving means to said first portion;

means for securing said first portion to said handle portion;

said handle portion sized to be received in an operator's hand and having a back side and an opposing front side having a digit engaging portion; wall means connecting said front side with said back side; said sides and wall means cooperating to define said chamber;

said wall means and back side having a thickness sufficient for said wall means and back side to be rigid in response to pressure applied by an operator's hand; said digit engaging portion of said front side having a thickness less than a thickness of said wall means and back side with said digit engaging portion resiliently flexible to flex toward said back side in response to a pressure applied by an operator's hand and return to a rest position when pressure is withdrawn;

means for supporting said pressure activated switch within said chamber with an activating element of said switch opposing an area of said digit engaging portion with said element spaced from said area a distance for said element not to be in activating engagement with said area when said engaging portion is in said rest position and to be in activating engagement with said area when said engaging portion is flexed in response to a pressure applied by an operator.

19. An apparatus according to claim 18 wherein said digit engaging portion has an area substantially greater than said area opposing said switch.

20. An apparatus according to claim 19 wherein said digit engaging portion has an area approximate to a range of motion of an operator's thumb opposing an operator's palm.

21. An apparatus according to claim 18 wherein said signal means comprises a sounder disposed within said chamber and having a sound generating surface opposing a surface of said handle portion said opposed surface having a plurality of holes therethrough and having a thickness sufficient for said surface to flex in response to pressure waves generated by said sounder.

22. An apparatus according to claim 21 wherein said opposed surface is an area of said front side and said digit engaging portion is disposed between said first portion and said sounder; said digit engaging portion comprising a depression formed on an outer surface of said front side with a liquid deflecting wall disposed between said depression and said surface opposing said sounder; said liquid deflecting wall tapered to direct a flow of liquid from said depression away from said surface opposing said sounder and off said front side.

23. An apparatus according to claim 18 comprising a raised ridge disposed on said housing between said first portion and said digit engaging portion.

24. An apparatus according to claim 23 wherein said raised ridge is disposed for an operator's digits to be aligned with said digit engaging portion when said handle portion is grasped by an operator's hand abutting said raised portion.

25. An apparatus according to claim 18 wherein said synthetic material is a polypropylene polymer.

26. An apparatus according to claim 25 wherein said material is a copolymer polypropylene polymer.

* * * * *